United States Patent [19]

Moran

[11] E Patent Number: Re. 32,701

[45] Reissued Date of Patent: Jun. 21, 1988

[54] NMR SCANNER WITH MOTION ZEUGMATOGRAPHY

[75] Inventor: Paul R. Moran, Winston-Salem, N.C.

[73] Assignee: Wisconsin Alumni Research Foundation, Madison, Wis.

[21] Appl. No.: 36,103

[22] Filed: Apr. 8, 1987

Related U.S. Patent Documents

Reissue of:

[64] Patent No.: 4,516,075
Issued: May 7, 1985
Appl. No.: 455,596
Filed: Jan. 4, 1983

[51] Int. Cl.[4] ..... G01R 33/20

[52] U.S. Cl. ..... 324/309; 324/306

[58] Field of Search ..... 324/300, 307, 309, 312, 324/306

[56] References Cited

U.S. PATENT DOCUMENTS

| | | | |
|---|---|---|---|
| 4,015,196 | 3/1977 | Moore et al. | 324/309 |
| 4,021,726 | 5/1977 | Garroway et al. | 324/309 |
| 4,070,611 | 1/1978 | Ernst | 324/309 |
| 4,115,730 | 9/1978 | Mansfield | 324/309 |
| 4,254,778 | 3/1981 | Clow et al. | 128/653 |
| 4,284,950 | 8/1981 | Burl et al. | 324/320 |
| 4,297,637 | 10/1981 | Crooks | 324/309 |
| 4,318,043 | 3/1982 | Crooks et al. | 324/309 |
| 4,319,190 | 3/1982 | Brown | 324/309 |
| 4,339,716 | 7/1982 | Young | 324/309 |
| 4,339,718 | 7/1982 | Bull et al. | 324/319 |
| 4,345,207 | 8/1982 | Bertrand et al. | 324/308 |
| 4,354,157 | 10/1982 | Feiner | 324/312 |
| 4,355,282 | 10/1982 | Young et al. | 324/309 |
| 4,431,968 | 2/1984 | Edelstein et al. | 324/309 |
| 4,443,760 | 4/1984 | Edelstein et al. | 324/309 |
| 4,451,788 | 5/1984 | Edelstein et al. | 324/309 |
| 4,471,305 | 9/1984 | Crooks et al. | 324/309 |
| 4,471,306 | 9/1984 | Edelstein et al. | 324/309 |
| 4,509,015 | 4/1985 | Ordidge et al. | 324/309 |
| 4,516,075 | 5/1985 | Moran | 324/309 |
| 4,528,985 | 7/1985 | Macovski | 128/653 |

OTHER PUBLICATIONS

"The NMR Blood Flowmeter–Theory and History", Battocletti et al., Med Phys. 8(4), Jul./Aug. 1981, pp. 435–443.

"Applications de la Resonance Magnetique Nucleaire en Hemodynamique(*)", A. Constantiensco et J. Chambron, (Jan. 23, 1981), pp. 127–134.

"NMR Rheotomography: Feasibility and Clinical Potential"–Grant et al., Med Phys. 9(2), Mar./Apr. 1982, pp.188–193.

Packer, K. J.; Rees, C. and Tomlinson, D. J., "A Modification of the Pulsed Magnetic Field Gradient Spin Echo Method of Studying Diffusion," Molecular Physics, 1970, vol. 18(3):421–423.

Kaufman, L. et al., "The Potential Impact of Nuclear Magnetic Resonance Imaging on Cardiovascular Diagnosis," Circulation, An Official Journal of the American Heart Association, Inc., Feb., 1983, 67(2):251–257.

Kaufman, Leon et al., "Evaluation of NMR Imaging for Detection and Quantification of Obstructions in Vessels," Investigative Radiology, Nov.-Dec., 1982, 17(6):554–560.

Hilal et al., "Special Project II–Studies of Two-Dimensional Blood Flow Using Nuclear Magnetic Resonance", a 377 page proposal submitted to the Dept. of Health, Education and Welfare, pp. 208–229.

J. R. Singer, "NMR Diffusion and Flow Measurements and An Introduction to Spin Phase Graphing", The Institute of Physics, pp. 281–291.

"Basic Concepts for Nuclear Magnetic Resonance Imaging"–Fullerton Magnetic Resonance Imaging, vol. 1, pp. 39–53, 1982.

Torrey, H. C., "Bloch Equations with Diffusion Terms", Phys. Rev., 1956, 104:563.

Singer, J. R., "Blood Flow Rates by NMR Measurements," Science, 1959, 130:1652.

Abragam, A., "The Principles of Nuclear Magnetism." London, Oxford University Press, 1961, pp. 58–63.

Stejskal and Tanner, "Spin Diffusion Measurements–," Jour. Chem. Phys., 1965, 42(1):288–292.

Stejskal, E. O., "Use of Spin Echoes in a Pulsed Magnetic Field Gradient to Study Anisotropic, Restricted Diffusion and Flow," Jour. Chem. Phys., 1965, 43(10):3597–3603.

Hahn, Erwin, "Detection of Sea-Water Motion by

Nuclear Precession," Jour. Geophys. Res., Feb., 1960, 65(2):776–777.
Packer, K. J., "The Study of Slow Coherent Molecular Motion by Pulsed Nuclear Magnetic Resonance," Molecular Physics, 1969, 17(4):355–368.
Grover, Thomas Peaks; Ph.D. Dissertation, Dept. EE, U.C. Berkeley (examiners Singer, Woodyard and Hahn), Jun. 15, 1971.
Hayward, R. J.; Packer, K. J.; Tomlinson, D. J., "Pulsed Field-Gradient Spin-Echo NMR Studies of Flow in Fluids," Molecular Physics, 1972, 23(6):1083–1102.
Garroway, G. N. "Velocity Measurements in Flowing Fluids by NMR," Jour. Phys. D: Appl. Phys., 1974, vol. 7, pp. L159–L163.
Libove, Joel, "Instrumentation for Imaging of Fluid Flow Using Nuclear Magnetic Resonance With an Example of One-Dimensional Flow Imaging," Doctoral Dissertation.
Fukuda and Hirai, "A Pulsed NMR Study of the Flow in Fluid," Journal of the Physical Society of Japan, Dec., 1979, 47(6):1999–2006.
Singer, J. R. and Crooks, L. E., "NMR Flow Imaging," Proc. Int. Symp. on NMR Imaging, Bowman Gray School of Medicine, Oct., 1981, pp. 185–190.
Mansfield, P. and Morris, P. G., "NMR Imaging in Biomedicine," pp. 235–238.
Van As, H, and Schaafsma, T. J., "Non-Invasive Blood Flow Measurements By the $^1$H NMR $\pi$-Pulse Method," Society of Magnetic Resonance in Medicine, First Annual Meeting, Aug. 16–18, 1982, Boston, Massachusetts, pp. 147–148.
Crooks, L. et al., "Physical Basis of Nuclear Magnetic Resonance Imaging," IEEE Transactions of Nuclear Science, vol. NS-29, Nos. 3, Jun., 1982, pp. 1252–1257.
Deville, G. and Landesman, A., "Experiences D'Echoes de Spins Dans Un Liquide En Ecoulement," Le Journal De Physique, Jan., 1971, pp. 67–72.
Grover, Thomas and Singer, J. R., "NMR Spin-Echo Flow Measurements," Journal of Applied Physics, Mar. 1, 1971, 43(3):938–939.
Grover, Thomas and Singer, J. R., "Recent Measurements of Flow Using Nuclear Magnetic Resonance Techniques," Modern Developments in Flow Measurements, Sep., 1971, pp. 38–46, Proc. the Harwell (Berks, England) Conference, Ed. CG Clayton (The Harwell Atomic Energy Establishment. Peter Perigrinin, Ltd., pub).
Pykett, I. L. and Mansfield, P., "A Line Scan Image Study of a Tumorous Rat Leg by NMR," Phys. Med. Biol., 1978, vol. 23, No. 5, pp. 961–967.
Hahn, E. L., "Spin Echoes," Physical Review, Nov. 15, 1950, vol. 80(4):580–594.
Carr, H. Y. and Purcell, E. M., "Effects of Diffusion on Free Precession in Nuclear Magnetic Resonance Experiments," May 1, 1954, vol. 94(3):630–639.

*Primary Examiner*—Michael J. Tokar
*Attorney, Agent, or Firm*—Quarles & Brady

[57] ABSTRACT

An NMR zeugmatographic scanner is modified to produce flow images. A motion sensitizing gradient field is applied to the gyromagnetic nuclei after transverse excitation and prior to emission measurement. The motion sensitized free induction signal which results is processed using an inverse Fourier transformation to produce a number of useful images.

30 Claims, 5 Drawing Sheets

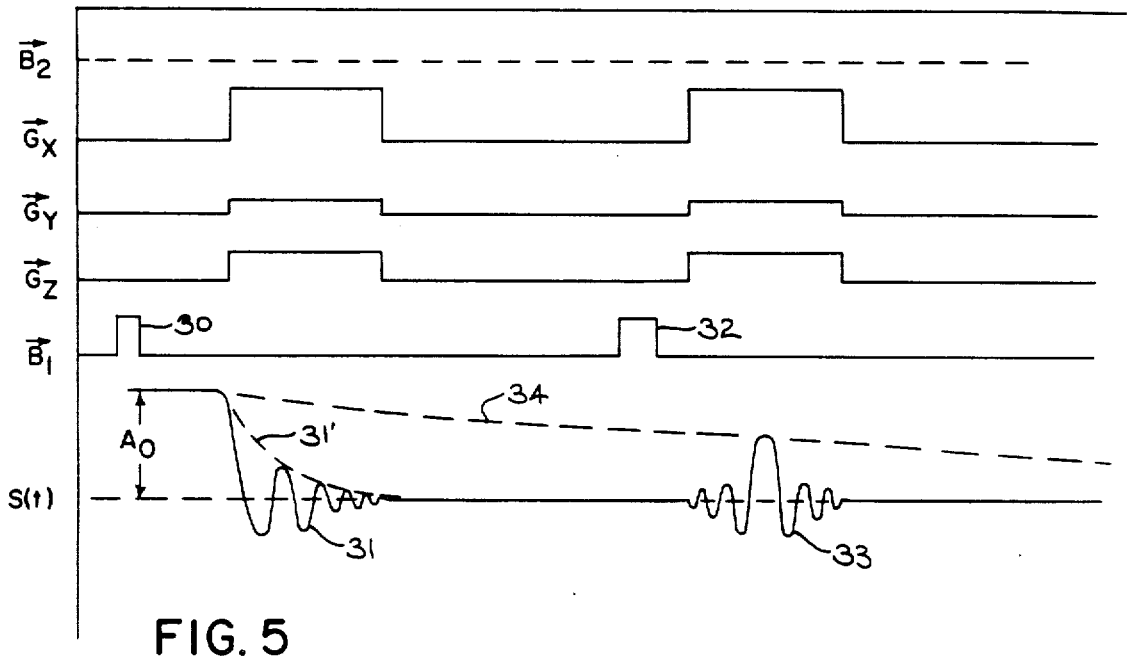
FIG. 5
FIG. 6
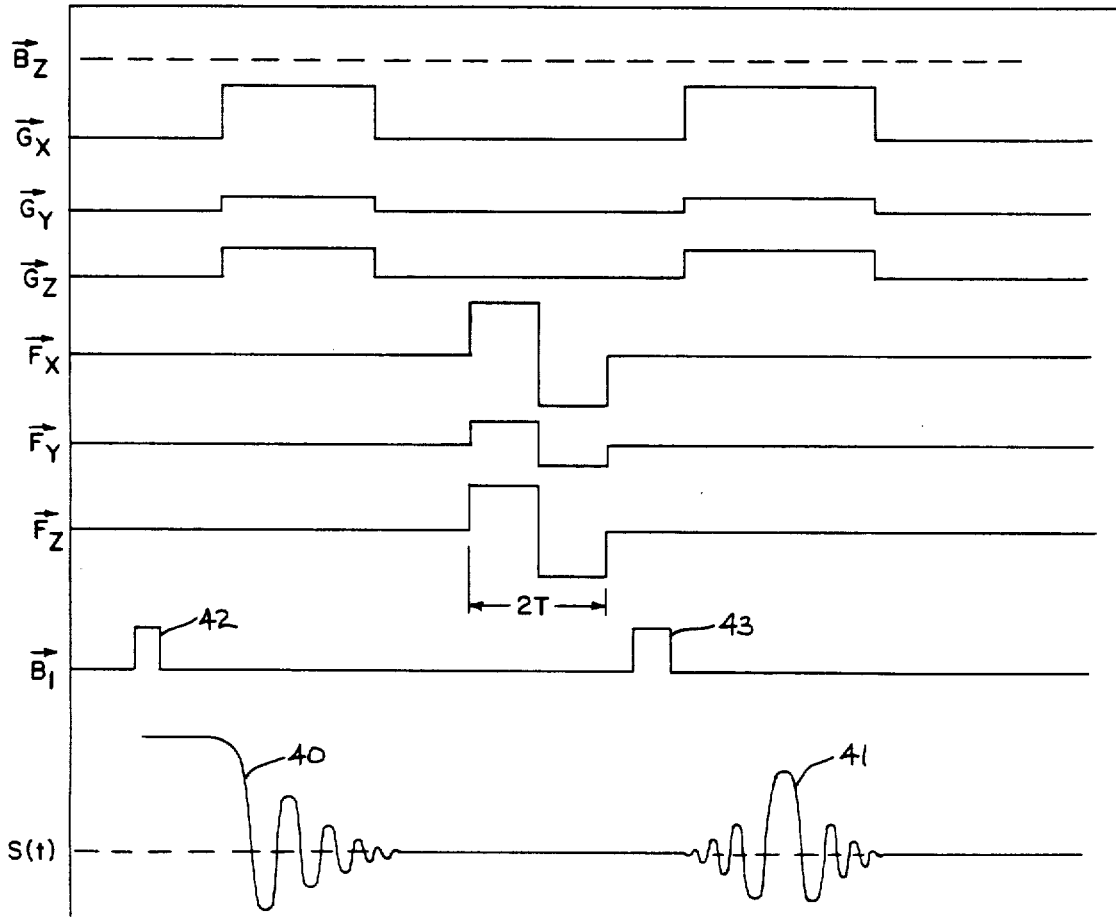

NMR SCANNER WITH MOTION ZEUGMATOGRAPHY

Matter enclosed in heavy brackets [ ] appears in the original patent but forms no part of this reissue specification; matter printed in italics indicates the additions made by reissue.

BACKGROUND OF THE INVENTION

The field of the invention is gyromagnetic resonance spectroscopy, and particularly, nuclear magnetic resonance (NMR) techniques for measuring the properties of materials.

Gyromagnetic resonance spectroscopy is conducted to study nuclei that have magnetic moments and electrons which are in a paramagnetic state. The former is referred to in the art as nuclear magnetic resonance (NMR), and the latter is referred to as paramagnetic resonance (EPR) or electron spin resonance (ESR). There are other forms of gyromagnetic spectroscopy that are practiced less frequently, but are also included in the field of this invention.

Any nucleus which possesses a magnetic moment attempts to align itself with the direction of the magnetic field in which it is located. In doing so, however, the nucleus precesses around this direction at a characteristic angular frequency ([Larmour] *Larmor* frequency) which is dependent on the strength of the magnetic field and on the properties of the specific nuclear species (the magnetogyric constant $\gamma$ of the nucleus).

When a substance such as human tissue is subjected to a uniform magnetic field (polarizing field $B_z$) the individual magnetic moments of the paramagnetic nuclei in the tissue attempt to align with this field, but precess about it in random order at their characteristic [Larmour] *Larmor* frequency. A net magnetic moment $M_z$ is produced in the direction of the polarizing field but the randomly oriented components in the perpendicular plane (x-y plane) cancel one another. If, however, the substance, or tissue, is irradiated with a magnetic field (excitation field $B_1$) which is in the x-y plane and which is near the [Larmour] *Larmor* frequency, the net aligned moment, $M_z$, can be rotated into the x-y plane to produce a net transverse magnetic moment $M_1$ which is rotating in the x-y plane at the [Lamour] *Larmor* frequency. The degree to which the rotation of $M_z$ into an $M_1$ component is achieved, and hence, the magnitude and the direction of the net magnetic moment ($M=M_0+M_1$) depends primarily on the length of time of the applied excitation field $B_1$.

The practical value of this gyromagnetic phenomena resides in the radio signal which is emitted after the excitation signal $B_1$ is terminated. When the excitation signal is removed, an oscillating sine wave is induced in a receiving coil by the rotating field produced by the transverse magnetic moment $M_1$. The frequency of this signal is the [Larmour] *Larmor* frequency, and its initial amplitude, $A_0$, is determined by the magnitude of $M_1$. The amplitude A of the emission signal (in simple systems) decays in an exponential fashion with time, t:

$$A=A_0e^{-t/T_2}.$$

The decay constant $1/T_2$ is a characteristic of the process and it provides valuable information about the substance under study. The time constant $T_2$ is referred to as the "spin-spin relaxation" constant, or the "transverse relaxation" constant, and it measures the rate at which the aligned precession of the nuclei dephase after removal of the excitation signal $B_1$.

Other factors contribute to the amplitude of the free induction decay (FID) signal which is defined by the $T_2$ spin-spin relaxation process. One of these is referred to as the spin-lattice relaxation process which is characterized by the time constant $T_1$. This is also called the longitudinal relaxation process as it describes the recovery of the net magnetic moment M to its equilibrium value $M_0$ along the axis of magnetic polarization (Z). The $T_1$ time constant is longer than $T_2$, much longer in most substances, and its independent measurement is the subject of many gyromagnetic procedures.

The measurements described above are called "pulsed NMR measurements." They are divided into a period of excitation and a period of emission. As will be discussed in more detail below, this measurement cycle may be repeated many times to accumulate different data during each cycle or to make the same measurement at different locations in the subject. A variety of preparative excitation techniques are known which involve the application of one or more excitation pulses of varying duration. Such preparative excitation techniques are employed to "sensitize" the subsequently observed free induction decay signal (FID) to a particular phenomena. Some of these excitation techniques are disclosed in U.S. Pat. Nos. 4,339,716; 4,345,207; 4,021,726; 4,115,730 and 3,474,329.

Although NMR [meansurements] *measurements* are useful in many scientific and engineering fields, their potential use in the field of medicine is enormous. NMR measurements provide a contrast mechanism which is quite different from x-rays, and this enables differences between soft tissues to be observed with NMR which are completely indiscernible with x-rays. In addition, physiological differences can be observed with NMR measurements, whereas x-rays are limited primarily to anatomical studies.

For most medical applications utilizing NMR, an imaging technique must be employed to obtain gyromagnetic information at specific locations in the subject. The foremost NMR imaging technique is referred to as "zeugmatography" and was first proposed by P. C. Lauterbur in a publication "Image Formation by Induced Local Interactions: Examples Employing Nuclear Magnetic Resonance", Nature, Vol. 242, Mar. 16, 1973, pp. 190–191. Zeugmatography employs one or more additional magnetic fields which have the same direction as the polarizing field $B_0$, but which have a nonzero gradient. By varying the strength (G) of these gradients, the net strength of the polarizing field $B_0=B_z+G_xX+G_yY+G_zZ$ at any location can be varied. As a result, if the frequency response of the receiver is narrowed to respond to a single frequency, $W_0$, then gyromagnetic phenomena, will be observed only at a location where the net polarizing field $B_0$ is of the proper strength to satisfy the [Larmour] *Larmor* equation; $W_0=\gamma B_0$: where $W_0$ is the [Larmour] *Larmor* frequency at that location.

By "linking" the resulting free induction signal FID with the strengths of the gradients ($G=G_x, G_y, G_z$) at the moment the signal is generated, the NMR signal is "tagged", or "sensitized", with position information. Such position sensitizing of the NMR signal enables an NMR image to be produced by a series of measurements.

The series of free induction decay signals produced during a scan of the subject are digitized and processed by a computer to extract their various frequency components for display on a screen. The most prevalent method involves the application of a discrete Fourier transform to the digitized NMR signals. Such transform may be in one or several variables as discussed in "The Fourier Transform and Its Applications", by R. N. Bracewall, published in 1978 by McGraw-Hill. Computer programs for performing such discrete Fourier transforms are well known, as discussed in "Fourier Analysis of Time Series: An Introduction", by P. Bloomfield, published in 1976 by Wiley. Two files of digital data are produced by the Fourier transformation of the time domain NMR signals. One file represents the "real" component and the second file represents the "imaginary" component. As discussed in U.S. Pat. No. 4,070,611 it can be demonstrated that the imaginary file is not required to reproduce an accurate image of the NMR phenomena of interest, and it is common practice to ignore this data.

The use of NMR to measure the flow of fluids in vessels is well known. A paper "The NMR Blood Flowmeter-Theory and History" by J. H. Battocletti et al, published in Medical Physics, Vol. 8, No. 4, July/August, 1981, describes the theory and history of this effort. The techniques heretofore employed to measure flow require special NMR apparatus with coils arranged to magnetize a sample of the fluid "upstream" of the coils which are employed to sense the FID signal. The physical distance between this "tagging" coil and the sensing coil is known, and the level of the FID signal provides velocity information in the direction of fluid flow. In an article "NMR Rheotomography: Feasibility and Clinical Potential", by J. P. Grant et al and published in Medical Physics, Vol. 9, No. 2, March/April 1982, imaging techniques are employed to provide a flow intensity distribution in a tube. Such techniques are limited to measuring flow in a known direction, and have been limited in practice to the measurement of flow in inanimate objects or to the measurement of blood flow in the arms and legs of animals.

SUMMARY OF THE INVENTION

The present invention relates to an NMR imaging apparatus, and particularly, to a method and means for sensitizing the NMR signals to provide not only the conventional NMR image, but also to provide data from which a motion image can be constructed. In a gradient imaging NMR scanner the invention includes the application of a motion sensitizing magnetic field gradient (F) after the excitation portion of each measurement cycle and prior to the emission portion of each cycle. The resulting free induction decay signals which are produced by a series of such measurements are processed by performing an inverse Fourier transform to produce conventional image data mixed with motion image data in the real and imaginary data files. These data files may be processed to produce spin-density images modulated by conventional NMR phenomena, such as $T_1$ and $T_2$ relaxation, or the motion data may be processed to produce an image of the motion alone, or the data files may be processed to produce an image of conventional NMR phenomena modulated by motion.

A general object of the invention is to measure the motion of gyromagnetic material at any location within a subject. Conventional zeugmatrographic scanners may easily be modified to provide motion data along with image data. Such modifications include the application of a motion sensitizing magnetic field gradient F during the measurment cycle. The free induction decay signal FID which is produced is "linked" to a position and to the motion of the gyromagnetic material at that position. The same processing employed on the image data alone can be employed to construct a motion image.

Another object of the invention is to measure motion in any direction at any position within the subject. A conventional zeugmatographic scanner capable of exciting a gyromagnetic response from a location within the subject is used to produce a motion sensitized response. Motion sensitization is accomplished with a magnetic field gradient $\vec{F}$ of alternating polarity which is applied for a period 2T after the excitation portion of the measurement cycle is completed. The direction of the field (whose gradient is $\vec{F}$) is the same as the polarizing field $B_z$, but its strength is graduated in the x, y and z directions to "tag" the flow data with a direction, as well as a magnitude and position.

Another object of the invention is to provide motion image data without significantly altering the NMR measurement cycle. The motion sensitizing field gradient $\vec{F}$ can either be added to each measurement cycle, or separate motion measurement cycles can be interlaced within standard NMR measurement cycles. In either case the numerous preparative excitation techniques and emission measurement techniques known to the art can be carried out with only minor modification. Independence of the motion measurements is maintained by providing that the integral of the field gradient $\vec{F}$ over the time period 2T is substantially zero. Although the motion sensitizing field $\vec{F}$ is thus separate and independent of the field gradient $\vec{G}$ used to position sensitize the NMR signals, the two fields may be generated using the same coils.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

BRIEF DESCRIPTION OF THE DRAWINGS

FIG. 5 is a graphic illustration of a typical conventional measurement cycle performed by the scanner of FIG. 1;

FIG. 6 is a graphic illustration of a typical measurement cycle performed according to the present invention;

DESCRIPTION OF THE PREFERRED EMBODIMENT

Figure 1:
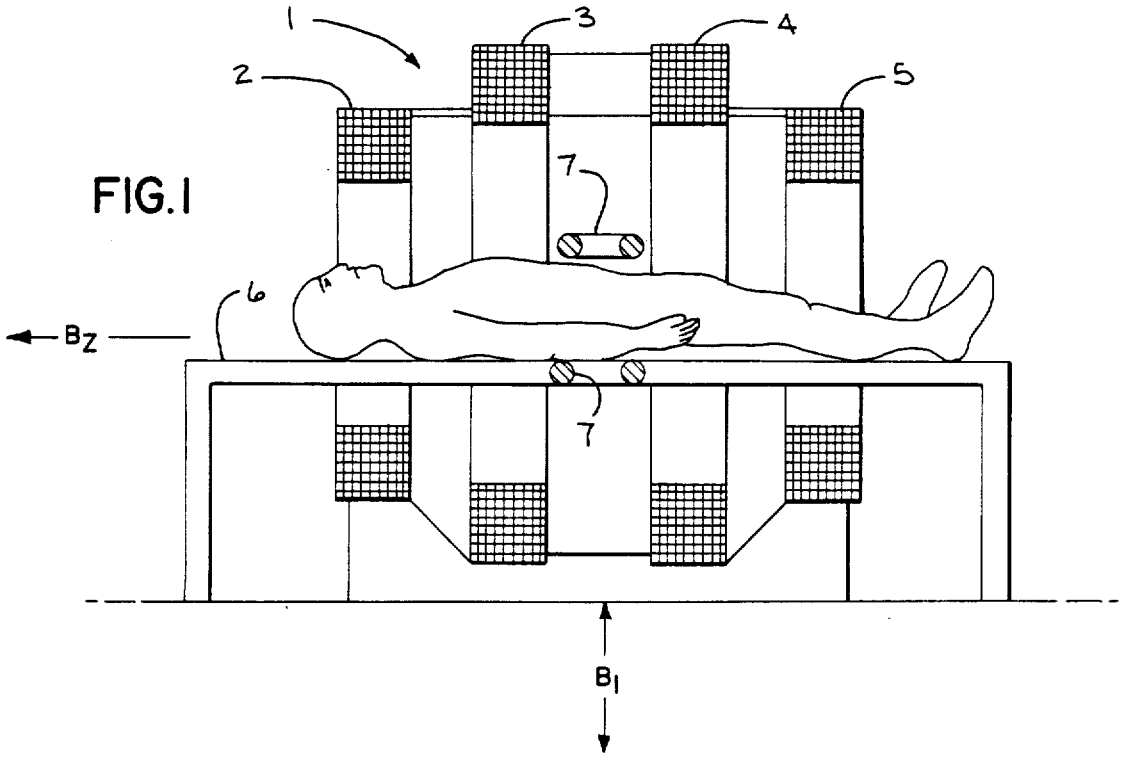
FIG. 1 is a schematic elevation view of an NMR scanner which employs the present invention.

Although the present invention may be easily implemented in a variety of gryromagnetic scanner [of] *or* NMR spectrometer structures, the preferred embodiment of the invention employs a large electromagnet to generate the polarizing field. Referring particularly to FIG. 1, this polarizing magnet 1 is comprised of four circular cylindrical segments 2–5 of sufficient size to receive a table 6. A patient may be placed on the table 6 and any portion of his body may be scanned by suitably positioning him with respect to excitation coils 7. The polarizing magnet 1 produces a strong magnetic field $B_z$ which is constant and homogeneous within the space defined by the excitation coils 7. The excitation coils 7 produce an excitation field $B_1$ which is in the transverse plane, perpendicular to the polarizing field $B_z$. The excitation field $B_1$ oscillates at a radio frequency $W_0$ and it is applied as one or more pulses. The coils 7 are then switched to a passive mode in which they operate as receivers for the NMR signals produced in the patient's body.

Figure 2A:
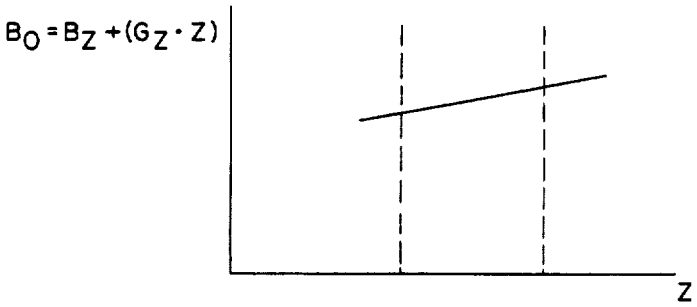
FIGS. 2A-2C are graphic illustrations of gradient magnetic fields produced in the scanner of FIG. 1.
Figure 3A:
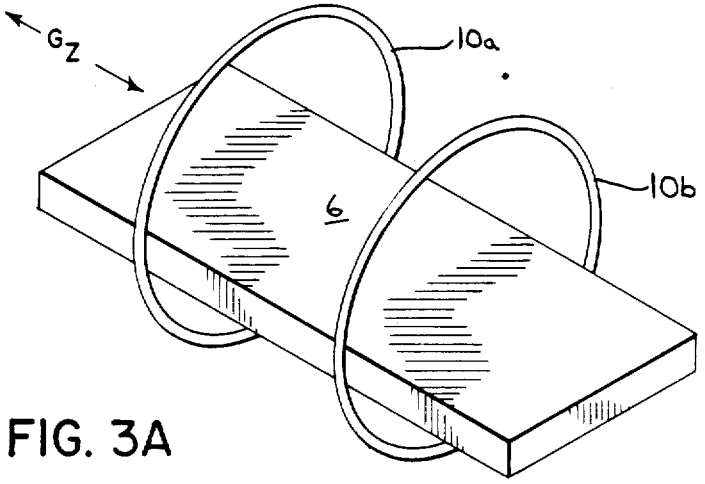
FIGS. 3A-3C are perspective views of the gradient coils which form part of the scanner of FIG. 1.
Figure 3B:
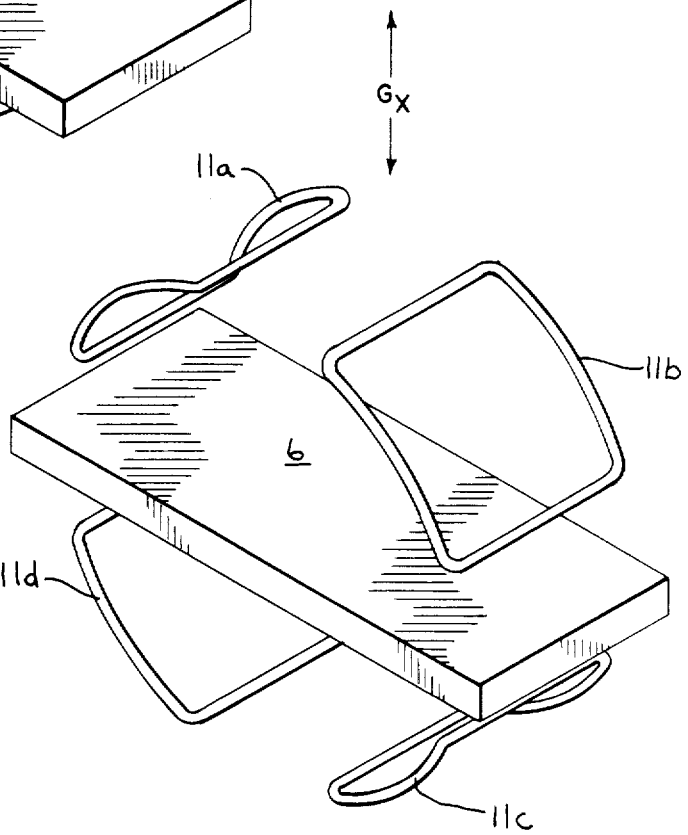
Figure 3C:
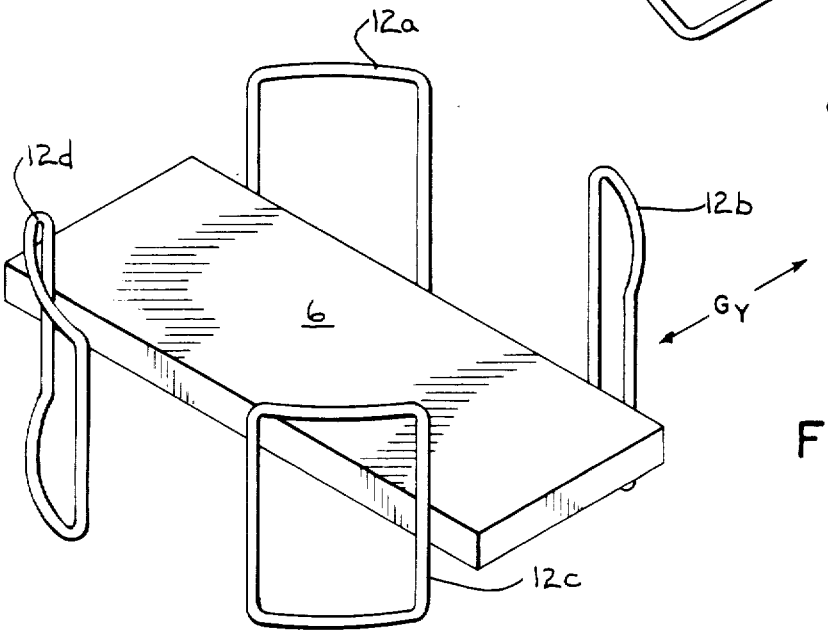

Referring to FIGS. 3A–3C, three sets of gradient field coils are also formed around the table 6. A set of Z gradient field coils 10*a* and 10*b* produce a magnetic field ($G_z$·Z) which is directed along the z axis of the machine, but which has a strength that changes as a function of position along the z axis. As shown in FIG. 2A, this field is additive to the polarizing magnetic field $B_z$ to provide a total field $B_0$ which varies in strength substantially linearly (i.e., $G_z$·Z) as a function of Z position on the table 6.

Figure 2B:
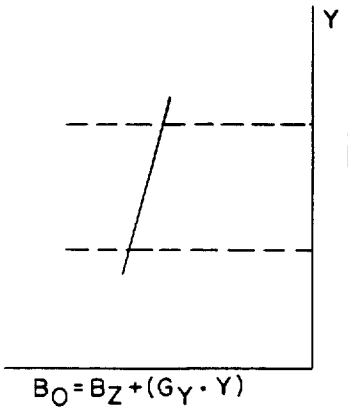

Referring to FIGS. 2B and 3B, a second set of gradient field coils 11*a*–11*b* produce a magnetic field ($G_x$·X) which is directed along the z axis of the machine, but which has a strength that changes as a function of position along the x axis. This field is additive to the polarization magnetic field $B_z$ to provide a total field $B_0$ which varies in strength substantially linearly as a function of x position on the table 6.

Figure 2C:
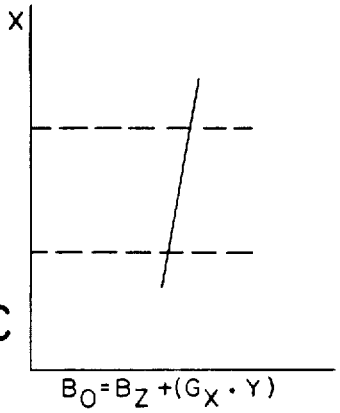

Referring to FIGS. 2C and 3C, a third set of gradient field coils 12a–12d produce a magnetic field ($G_y$·Y) which is directed along the z axis of the machine, but which has a strength that changes as a function of position along the y axis. This field is additive to the polarizing magnetic field $B_z$ to provide a total field $B_0$ which varies in strength substantially linearly as a function of y position on the table 6.

The generation and control of the polarizing magnetic field $B_z$ and the field gradients $G_x$, $G_y$ and $G_z$ is well known in the art and is employed in existing NMR scanners.

Figure 4:
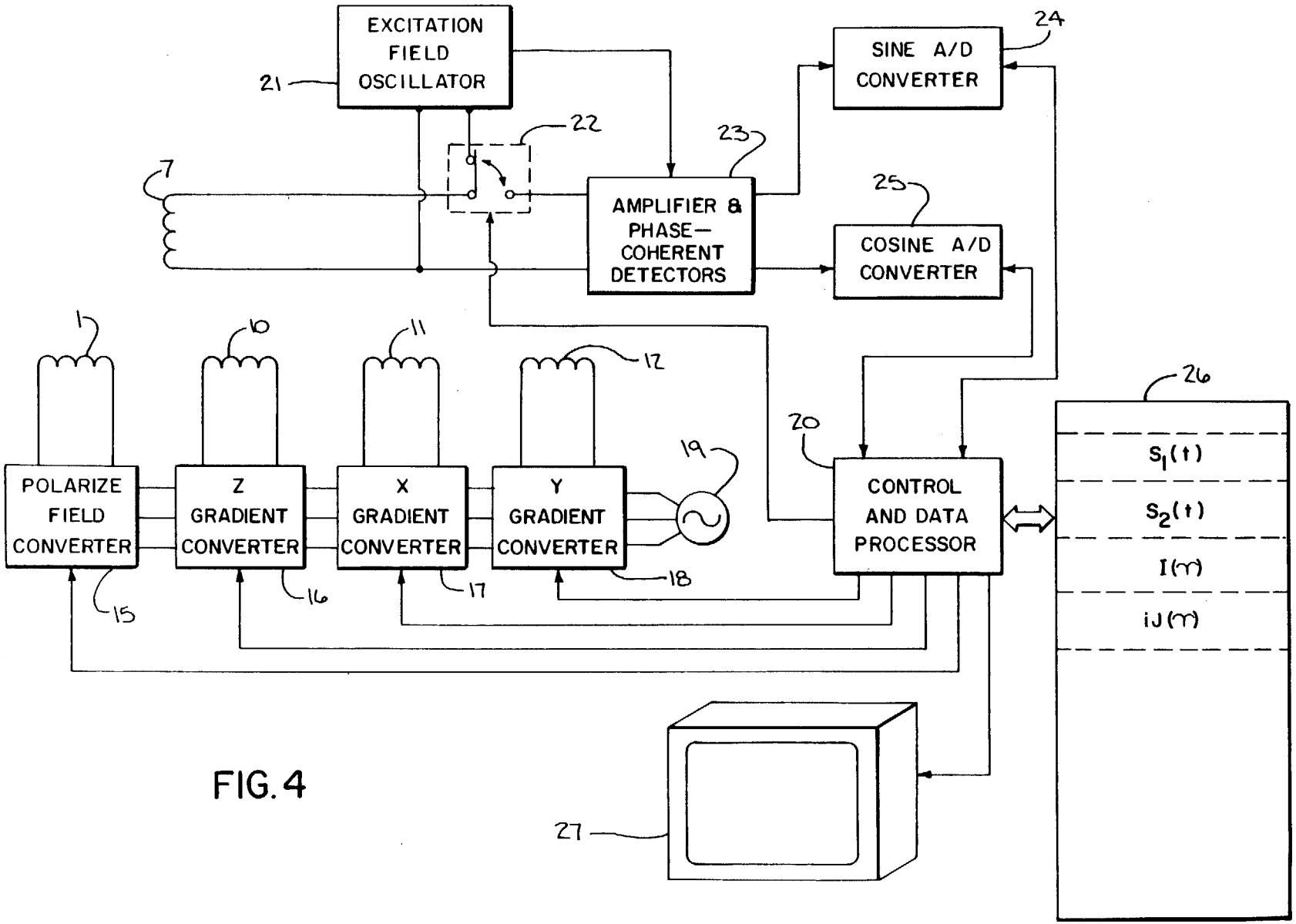
FIG. 4 is an electrical block diagram of the control system which forms part of the scanner of FIG. 1.

Referring particularly to FIG. 4, the control system for the NMR scanner includes a set of four static power converters 15–18 which connect to an a.c. power source 19. The static power converters 15–18 produce d.c. currents for the respective coils 1, 10, 11 and 12 at levels determined by commands received from a processor 20. The polarity, or direction, of the d.c. currents produced for the gradient field coils 10–12 can also be controlled. Thus, both the magnitude and the direction of the gradient fields in the x, y and z direction can be switched on command from the processor 20.

The excitation winding 7 is driven by a radio frequency oscillator 21 when an electronic switch 22 is toggled to its active position. The switch 22 is controlled by the processor 20 and when the switch 22 is toggled to its passive position, the excitation winding 7 is coupled to the input of an amplifier and phase-coherent detector circuit 23. The NMR signals in the patient induce a voltage in the excitation winding 7 which is amplified and demodulated in the circuit 23. The oscillator 21 provides a reference signal to the circuit 23 that enables one phase-coherent detector therein to produce an in-phase, or sine, free induction decay (FID) signal to an analog-to-digital converter 24. A second phase-coherent detector produces an orthogonal, or cosine, FID signal to an analog-to-digital converter 25.

The free induction decay signals produced by the phase-coherent detector 23 are digitized by the A/D converters 24 and 25. The sample rate of this digitization is controlled by the processor 20, and the digital numbers which are produced by the A/D converters 24 and 25 are input to a processor 20 and stored in a memory 26. The processor 20 also stores values indicative of the gradient field strengths at the moment the FID signals are produced, and in this manner, the FID signals are linked to a specific position within the patient.

Referring particularly to FIG. 5, a typical measurement cycle for the NMR scanner in its imaging mode is illustrated. Such measurement cycles are repeated many times during a single scan, with the strengths of the field gradients $G_x$, $G_y$ and $G_z$ being changed for each measurement to obtain the desired NMR response from a series of points in the subject. In the example cycle of FIG. 5 a first transverse excitation pulse 30 at the desired Larmour frequency is applied and the field gradients $G_x$, $G_y$ and $G_z$ are switched on at their desired levels. The length of the excitation pulse 30 is selected to provide maximum transverse magnetization (90°) of the gyromagnetic nuclei, and the resulting free induction decay signal 31 has an amplitude $A_0$. The rate at which the FID signal 31 decays (as indicated by dashed line 31') is a measure of the frequency distributions of the gyromagnetic nuclei excited in the subject by the field gradients ($G_x$, $G_y$, $G_z$).

To measure the $T_2$ relaxation time within the same measurement cycle, a second excitation pulse 32 is applied. This pulse 32 is at the same [Larmour] *Larmor* frequency, but it is twice as long as the pulse 30, and phase-shifted by 90°, with the result that the transverse magnetization is rotated 180°. This "echo" pulse stimulates the free induction decay signal 33 after the field gradients $G_x$, $G_y$ and $G_z$ are again applied. The peak value of this FID signal 33 is less than the value $A_0$ of the first FID signal 31, and as indicated by dashed line 34, it provides an indication of the $T_2$ relaxation time.

It should be apparent to those skilled in the art that the NMR measurement cycle illustrated in FIG. 5 is but one of many possible measurements that can be performed by the scanner system of FIG. 4. With this particular cycle, a number of images can be constructed which are of medical significance. Since the measurement variables such as gradient field strengths, and excitation pulse generation are under control of the processor 20, the NMR scanner system can be programmed to carry out any number of different measurement cycles.

Referring again to FIG. 4, the digitized representations of the FID signals generated during the complete scan are stored in the memory 26 as two files $S_1(t)$ and $S_2(t)$. $S_1(t)$ is that portion of the FID signal S(t) which is phase-referenced to the "cosine" phase of the transverse excitation signal produced by oscillator 21, and $S_2(t)$ is the "sine" phase. $S_1(t)$ and $S_2(t)$ may be combined to form the complex signal.

$$S(t)=S_1(t)+iS_2(t). \quad (1)$$

This may be written as the spectral transform:

$$S(t)=K\int m(w)e^{iwt}dw, \quad (2)$$

where:

$$w=w(\text{Larmor})-W_{rf},$$

and K is a constant electronic conversion factor. This signal has been spacially modulated by the field gradient $(\vec{G}=G_x\hat{x}+G_y\hat{y}+G_z z)$ and is equivalent to the following:

$$\begin{aligned}&[S(t)=\int M_1(r)e^{-2\pi i\gamma\vec{G}\cdot\vec{r}dr}]\\ &S(t)=\int M_1(r)e^{-2\pi i\gamma\vec{G}\cdot\vec{r}}dr\end{aligned} \quad (3)$$

where:
$M_1$ = transverse magnetization
$\vec{r}$ = a position (x, y, z)
$\gamma$ = magnetogyric constant.
This can be expressed in "q" space as:

$$\begin{aligned}&[S(q)=K\int M_1(r)e^{-2\pi i\vec{q}\cdot\vec{r}dr}]\\ &S(q)=K\int M_1(r)e^{-2\pi i\vec{q}\cdot\vec{r}dr}\end{aligned} \quad (4)$$

where: "$\vec{q}$" is a position in three-dimensional space which is determined by the field gradient $\vec{G}$, $\vec{q}=\gamma\vec{G}t$.

Each measurement cycle thus produces a line sampling in q-space, and the data files $S_1(t)$ and $S_2(t)$ represent a set of such line samplings. An image $I_m(r)$ can be reconstructed from this data by performing a numerical discrete Fourier inversion to the desired geometry:

$$\begin{aligned}&[I_m(\vec{r})q=K\int H(q)S(q)e^{2\pi i\vec{q}\cdot\vec{r}dq}]\\ &I_m(\vec{r})=K\int H(q)S(q)e^{2\pi i\vec{q}\cdot\vec{r}dq}\end{aligned} \quad (5)$$

Where: H(q) is the apodizing function associated with the digitizing process.

When the Fourier inversion is performed according to equation (5) by the processor 20, two data files are created, I(r) and iJ(r), where:

$$I_m(\vec{r})=I(\vec{r})+iJ(\vec{r}). \quad (6)$$

It is well known in the art that the image data in the file I(r) may be output to a display device, such as the CRT 27 in FIG. 4, to produce an image. Such an image may represent primarily the density of the excited gyromagnetic nuclei ("spin-density") or the image may be modulated by $T_1$ or $T_2$ factors to provide improved contrast of the anatomical or [psysiological] *physiological* phenomenon. The "imaginary" data file iJ(r) returns a null-value when the system is properly tuned, and it is usually discarded in prior NMR scanner systems.

Although spin-density, $T_1$ and $T_2$ images provide useful information of an anatomical nature, the present invention enables a motion image to be produced. The flow of fluids in a human subject is a most important phenomena, and its measure and imaging provides diagnostic medicine with invaluable information for functional assessment and physiological status. Although the "motion-zeugmatographic" imaging method and system of the present invention may be employed to image acceleration, jerk, etc., its primary value to medicine is believed to be in the production of velocity images.

Referring particularly to FIG. 6, the present invention may be implemented as part of a conventional NMR measurement cycle. After a first free induction decay signal 40 is received and digitized in the standard manner described above, a motion sensitizing field gradient, $$\vec{F}=F_x\hat{x}+F_y\hat{y}+F_z\hat{z}$$

is applied to the subject. This motion sensitizing field gradient may be generated with the gradient field coils 10–12 (FIG. 3), and it is characterized by the fact that it alternates in polarity such that its integral is equal to zero over its time period 2T.

$$\int F(t)dt=0.$$

The relative values of the coordinate components $F_x$, $F_y$, $F_z$ determine the direction in which the subsequent NMR signal 41 is motion sensitized.

The measurement cycle illustrated in FIG. 6 may be repeated many times to motion sensitize a series of NMR signals 41 in many directions. The set of motion sensitized data which results from this series of "F cycles" is stored, and the gradient fields $G_x$, $G_y$ and $G_z$ are then changed to position sensitize the next series of F cycles to a different location in the subject. The process is continued with a series of motion sensitized measurements being made at each location in the scan.

It is a requirement of the present invention that the motion sensitizing field gradient $\vec{F}$ be applied after the application of an excitation field which produces a transverse magnetic moment $M_1$. Furthermore, motion sensitization must occur prior to the emission of the FID signal which it is to sensitize. In the example measurement cycle of FIG. 6, excitation pulse 42 produces the required transverse magnetic moment $M_1$. The flow sensitizing field gradient $\vec{F}$ is applied after the first free induction signal 40 is produced, and hence the data which is collected from the FID 40 is not motion sensitized. The FID signal 41 on the other hand, is produced by "echo" excitation pulse 43 after the motion sensitizing field gradient $\vec{F}$ has been applied. It contains motion information. In this example the echo excitation pulse 43 does not produce any additional transverse magnetic moment $M_1$.

Figure 7:
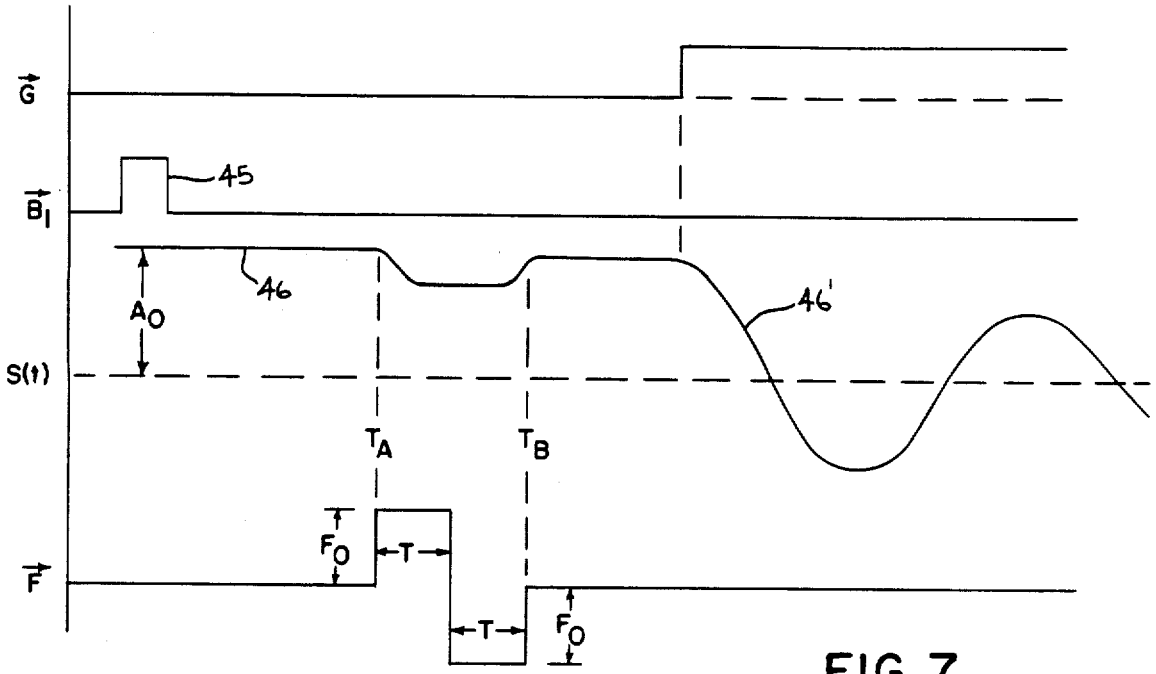
FIG. 7 is a graphic illustration of a portion of an alternative measurement cycle according to the present invention.

Another possible measurement cycle which produces motion sensitized data is illustrated in FIG. 7. In this cycle a 90° excitation pulse 45 is applied to produce maximum transverse magnetic moment and the position gradient field $\vec{G}$ is later switched on to produce the free induction decay signal 46. At time $T_A$ during the generation of the FID 46, a motion sensitizing field gradient $\vec{F}$ is applied until time $T_B$. The FID signal 46' (generated after $T_B$) is motion sensitized.

The direction of the motion which is measured is determined by the direction of the field gradient $\vec{F}$. The measurement sensitivity is determined by a number of factors, including the strength ($F_0$) of the field gradient $\vec{F}$ and its duration (2T). If the systematic phase errors produced by the system are denoted by "e", then the minimum velocity which can reliably be measured is as follows:

$$V_{min}=e[2\pi\gamma F_0T^2]^{-1} \quad (7)$$

where e is in radians.

For example, if the motion of hydrogen nuclei is measured with a system having a phase resolution error of $e=0.1$ radian, then the following conditions are typical:

$$y=4.6\times10^{-3}H_z/\text{gauss}$$

$$T=10\text{ msec.}$$

$$F_0=0.5\text{ gauss/cm.}$$

$$V_{min}=0.06\text{ cm./second.}$$

It should be apparent that the measurement process can be shortened and simplified considerably if fluid flow in only one direction is imaged. For example, if only the motion sensitizing field gradient $F_z$ is employed, an average velocity image of fluid flow along the z axis is generated. In such case, only one flow sensitized measurement is required at each "G" position of the scan.

The flow sensitized FID signal [at] *is* both position and motion sensitized. As indicated above in equation (3), the digitized FID signal S(t) which is stored in the memory 26 is linked to position by the gradient field $\vec{G}$. Similarly the motion sensitized FID signal S(t) is linked to the velocity of the spin-density at this same position by the motion field gradient $\vec{F}$:

$$S(t)=\int\int M_1(r,v)e^{2\pi\gamma[\vec{G}\cdot\vec{r}t+\vec{F}\cdot\vec{v}(T)^2]}drdv \quad (8).$$

If a six-dimensional discrete Fourier inversion is performed on this stored data file, an image $\Delta(r,v)$ can be constructed on the CRT 27 which displays spin-density ($p_0$) distributed according to the proportions of that density possessing particular velocities in the direction F of the gyromagnetic nuclei at that location.

$$\Delta(\vec{r},\vec{v})=K\int\int H(q)H(f)S(q,f)e^{2\pi i(\vec{q}\cdot\vec{r}+\vec{f}\cdot\vec{v})}dqdf \quad (9)$$

where: H(q) and H(f) are apodizing functions associated with digitizing the FID and "f" is a position in three-dimensional Fourier-velocity space which is determined by the velocity field gradient $\vec{F}$, where $\vec{f}=\gamma\vec{F}(T^2)$.

This six-dimensional image, $\Delta(\vec{r},\vec{v})$, is the most general and ambitious direct image of true flow velocities since it enables many points in "f" space to be measured by sensitizing a series of FID signals with velocity gradients $\vec{F}$ having different directions and different magnitudes. The technique can be considerably simplified if the image is modulated by a single velocity gradient $\vec{F}$ at each point. This considerably shortens the data collection portion of the process since it requires only one $\vec{F}$ cycle for each $\vec{G}$ cycle, but it returns only the average velocity of flow rather than a complete velocity distribution scale, or profile.

There is an endless variety of modifications and simplications by which the motion-zeugmatographic phase-modulation method of the present invention can be applied to studies of practical importance. Chemical shift distributions or $T_1$ and $T_2$ spectroscopy may be added and similarly "interlaced" in the data-collection cycle. The $B_1$ excitation field may be modulated to suppress or isolate contributions to the $T_2$-process, and as will be described in more detail below, variations in the shape of the motion sensitizing field gradient F are possible.

As indicated above (equation (5)), the Fourier inversion performed on a conventional zeugmatographic NMR scanner returns data in a "real" file I(r) from which an image of spin-density $p_0(r)$ can be produced on the CRT 27. As indicated above by equation (9), when the Fourier inversion is performed on motion sensitized NMR data, the real file I(r) is returned with data which enables an image of spin-density $p_0(r)$ modulated by velocity V(r) to be produced on the CRT 27.

It is another aspect of the present invention that when the Fourier inversion of flow sensitized NMR data is performed, the "imaginary" data file iJ(r) returns information from which images of particular medical value can be produced. More specifically, if the NMR data is flow sensitized in a single direction (i.e., one $\vec{F}$ cycle per $\vec{G}$ cycle), and if the magnitude ($F_0$) and duration (2T) of the flow sensitizing field gradient field are kept small such that:

$$e^{i2\pi\gamma T^2\vec{F_0}\cdot\vec{V}}\simeq1+i2\pi\gamma T^2\vec{F_0}\cdot\vec{V} \quad (10)$$

the real file I(r) returns conventional image data $p_0(r)$. However, the imaginary file iJ(r) now returns image data:

$$J(r)=(2\pi\gamma T^2\vec{F}_0)\cdot[p_0(\vec{r})(\vec{V})] \quad (11).$$

The values in parentheses are known measurement conditions and $p_0(\vec{r})$ is precisely the set of values returned in the real life I(r). Consequently, a velocity image V(r) can be produced on the CRT 27 as follows:

$$V(r)=J(r)/[(2\pi\gamma T^2F_0)I(r)] \quad (12).$$

Thus in a single scan of the subject, data files $S_1(t)$ and $S_2(t)$ can be created and stored in the memory 26. From the files I(r) and iJ(r) which are produced by the Fourier inversion of these data files, three separate images can be produced with [mineral] *minimal* computation. The first image $p_0(r)$ is the conventional spin-density NMR image as modulated by phenomena such as $T_1$ and $T_2$. The second image is the same spin-density image $p_0(r)$ modulated by the magnitude of average spin velocity V(r) in the direction selected by the flow sensitizing field gradient $\vec{F}$. The third image is the magnitude of spin velocity V(r) in the direction of $\vec{F}$ throughout the region of the NMR scan.

It should be apparent to those skilled in the art that other images of medical value can be constructed from this measured data with further computation. For example, the exchange flow of molecules into or out of a specified volume may be calculated by integrating the velocity modulated spin-density values $\Delta(\vec{r},\vec{v})$ over the surface area of the volume. The same flow rate through a specified plane may also be calculated by integrating across the surface of the plane. Such measurements may provide, for example, the quantity of blood flowing through a specific vessel. It is important to note that because an anatomical image may be produced from the same data, the location $(\vec{r})$ of the particular volume or surface of interest in the patient can be prescisely located by the NMR scanner operator.

Figure 8A:
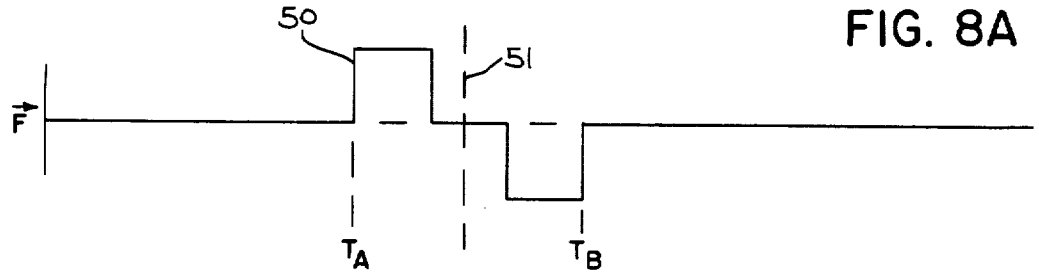
FIGS. 8A-8C are graphic illustrations of alternative forms of the motion sensitizing field gradient $\vec{F}$ which may be employed in the measurement cycles of FIGS. 6 and 7.
Figure 8B:
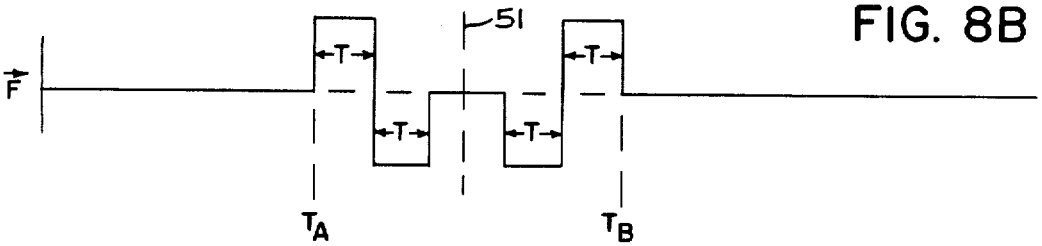

While the most important application of the invention is presently believed to be the measurement of velocity, the invention may be extended to measure "higher order" motion such as acceleration. For velocity sensitization, the flow sensitizing field gradient $\vec{F}$ must not only be of alternating polarity, but its wave form should be symmetrical. That is, the velocity sensitizing field gradient $\vec{F}$ should be a mirror image about horizontal and vertical axes of symmetry. Referring to FIG. 8A, for example, the field gradient wave form 50 alternates in polarity and is anti-symmetrically mirrored about an axis of symmetry 51. Needless to say, the integral of this wave form 50 over the interval $T_A$ to $T_B$ is zero and it therefore satisfies the basic requirement for motion sensitization. In contrast, the motion sensitization gradient field $\vec{F}$ produced by the wave form 52 in FIG. 8B is symmetrically mirrored about the vertical axis 51. This wave form will sensitize the subsequent NMR signal to acceleration. Note that the integral of the wave form 52 over the time period $T_A$ to $T_B$ is zero, thus satisfying the basic motion sensitization requirement.

Figure 8C:
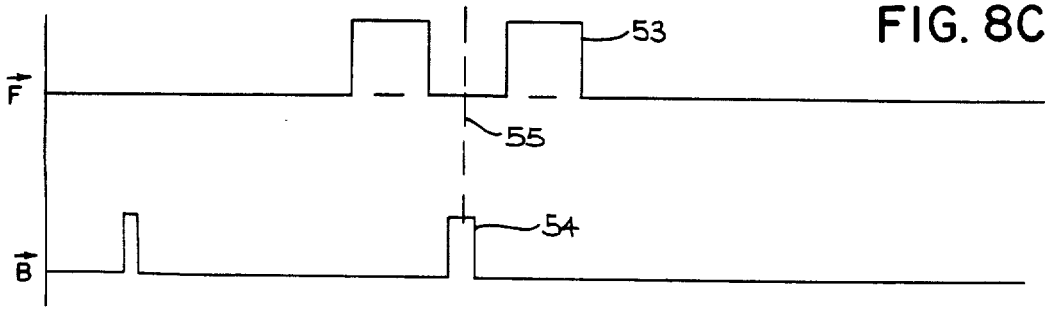

It should also be understood that the alternating polarity requirement for the motion sensitizing field gradient $\vec{F}$ is referenced to the gyromagnetic nuclei—not the table 6. Thus, if a 180° echo pulse of excitation energy is applied to the gyromagnetic nuclei, their phase-polarity is effectively reversed and the second half-cycle of the motion sensitizing field gradient $\vec{F}$ need not be reversed in polarity. This is illustrated in FIG. 8C, where the wave form 53 of the field $\vec{F}$ is the equivalent of the wave form 50 in FIG. 8A, when an echo pulse 54 is generated at the axis of symmetry 55. This technique may be useful with systems which do not enable the gradient fields to be reversed in polarity.

I claim:

1. In a gyromagnetic resonance instrument *for producing an image of an extended subject which contains both stationary gyromagnetic material and moving gyromagnetic material, in* which *the instrument* performs a measurement cycle by applying a transverse excitation signal to a gyromagnetic material and to thereby impart a transverse magnetic moment thereto, and which produces a FID signal responsive to emissions by the transversely magnetized gyromagnetic material, the improvement comprising:

*means for locating the position of the gyromagnetic material within the extended subject which is producing a FID signal;* means for motion sensitizing a FID signal in which a motion sensitizing magnetic field gradient $\vec{F}$ is applied to the gyromagnetic material for a period of time 2T after its transverse excitation and prior to the production of the FID signal, and wherein the motion sensitizing magnetic field gradient $\vec{F}$ has alternating polarity with respect to the gyromagnetic material such that its integral over the time period 2T is substantially zero; and detector means for receiving the FID signal and producing therefrom a signal $S_1(t)$ which is phase-referenced to the cosine phase of the transverse excitation signal and a signal $S_2(t)$ which is phase-referenced to the sine phase of the transverse excitation signal.

2. The instrument as recited in claim 1 in which the motion sensitizing magnetic field gradient $\vec{F}$ is substantially anti-symmetrical with respect to time T during the time period 2T.

3. The instrument as recited in claim 1 *in* which *the means for locating* includes means for applying a magnetic field gradient $\vec{G}$ to the gyromagnetic material such that the FID signals which are emitted from a selected location [therein] *in the extended subject* are [frequency] encoded during each measurement cycle and the motion sensitized FID signals are thereby also position sensitized.

4. The instrument as recited in claim 3 in which the means for generating said field gradients $\vec{G}$ and $\vec{F}$ both employ the same set of gradient coils which are positioned around the gyromagnetic material.

5. The instrument as recited in claim 1 which includes:

processor means for performing an inverse Fourier transform on the $S_1(t)$ and $S_2(t)$ signals to produce data indicative of motion intensity in the direction of the magnetic field gradient $\vec{F}$.

6. The instrument as recited in claim 1 in which the [direction and magnitude] *value* of the motion sensitizing magnetic field gradient $\vec{F}$ is altered for successive measurement cycles to produce a corresponding set of motion sensitized FID signals, and corresponding sets of $S_1(t)$ and $S_2(t)$ signals, and which includes:

processor means for receiving the sets of $S_1(t)$ and $S_2(t)$ signals and performing an inverse Fourier transform thereon to produce a corresponding set of output data indicative of motion intensity in the [directions] *direction* of the magnetic field gradient $\vec{F}$; and display means connected to receive the output data and produce an image.

7. A method for producing *from a gyromagnetic material* a FID signal which contains [motion] information *pertaining to the density of the gyromagnetic material and information pertaining to the acceleration of the gyromagnetic material, which information may be used to reconstruct an image,* the steps comprising:

applying a polarizing magnetic field to the gyromagnetic material;

exciting the gyromagnetic material with a magnetic field $B_1$ to produce a transverse magnetic moment $M_1$ therein;

applying a motion sensitizing magnetic field gradient $\vec{F}$ to the gyromagnetic material for a period *of time from 0 to* 2T after its transverse excitation, wherein the polarity of the field gradient $\vec{F}$ alternates with respect to the gyromagnetic material such that the integral of the field gradient $\vec{F}$ over the period 2T is substantially zero; *and such that the field gradient $\vec{F}$ is symmetrical about the time T;* and sensing *both the amplitude and the phase of* the FID signal produced by the transversely excited gyromagnetic material over a period of time after the time [period] 2T.

8. The method as recited in claim 7 in which a position sensitizing magnetic field gradient $\vec{G}$ is applied to the gyromagnetic material while the FID signal is being produced.

9. The method as recited in claim 7 which includes:

processing the FID signal by performing an inverse Fourier transform thereon; and displaying the processed FID signal.

10. An NMR scanner, the combination comprising:

means for generating a polarizing magnetic field $B_0$ within a gyromagnetic material;

means for generating an excitation magnetic field $B_1$ which produces a transverse magnetic moment in the gyromagnetic material;

means for sensing a FID signal produced by the gyromagnetic material excited by said excitation magnetic field $B_1$;

means for generating a position magnetic field gradient $\vec{G}$ in the gyromagnetic material to position sensitize the sensed FID signal and to thereby link the sensed FID signal to a location within the gyromagnetic material;

means for generating a motion magnetic field gradient $\vec{F}$ in the gyromagnetic material to motion sensitize the sensed FID signal and to thereby link the sensed FID signal to the motion of the gyromagnetic material at said location; and processor means for receiving sensed FID signals and producing an image which is modulated by the motion of the gyromagnetic material.

11. The NMR scanner as recited in claim 10 which includes control means for cyclically generating a series of said FID signals, said control means including:

means for altering the position magnetic field gradient $\vec{G}$ during successive cycles to link the series of FID signals with a succession of different locations in the gyromagnetic material.

12. The NMR scanner as recited in claim 11 in which the control means alters the motion sensitizing magnetic field gradient $\vec{F}$ during successive cycles to link a series of FID signals at a specific location in the gyromagnetic material to a succession of different motion values.

13. The NMR scanner as recited in claim 10 in which the means for generating the motion sensitizing magnetic field gradient $\vec{F}$ includes control means for producing the field $\vec{F}$ during each measurement cycle over a period of time 2T with alternating polarity such that the integral of F over the time period 2T is substantially zero.

14. In an NMR scanner which produces images related to the density distribution of a gyromagnetic phenomena is a gyromagnetic material, the improvement therein comprising:

means for motion sensitizing NMR signals produced by the gyromagnetic material, such sensitizing including the application of a magnetic field gradient $\vec{F}$ of alternating polarity *with respect to the gyromagnetic material*; and means for receiving the motion sensitized NMR signals and producing image data which is related to the density distribution of the gyromagnetic phenomena in the material and which is modulated by the motion of the gyromagnetic material.

15. The NMR scanner as recited in claim 14 which includes processor means for receiving said image data and producing an image which is related to the motion of the gyromagnetic material, but which is substantially independent of the density distribution of the gyromagnetic phenomena.

16. The NMR scanner as recited in claim 14 which includes processor means for receiving said image data and being operable to produce a first data file containing data for the production of an image related to the density distribution of the gyromagnetic phenomena, and being operable to produce a second data file containing data for the production of an image related to the density distribution of the gyromagnetic phenomena modulated by the motion of the gyromagnetic material.

*17. The instrument as recited in claim 1 in which the motion sensitizing magnetic field gradient $\vec{F}$ is substantially symmetrical with respect to time T during the time period 2T.*

*18. An NMR scanner, the combination comprising:*

*means for generating a polarizing magnetic field $B_0$ within a gyromagnetic material;*

*means for generating an excitation magnetic field $B_1$ which produces a transverse magnetic moment in the gyromagnetic material;*

*means for sensing both the amplitude and phase of a FID signal produced by the gyromagnetic material excited by said excitation magnetic field $B_1$;*

*means for generating a magnetic field gradient to produce a position phase sensitizing field gradient $\vec{G}$ which imparts a first phase component in the FID signal that indicates the position of the gyromagnetic material which is producing the FID signal;*

*means for generating a magnetic field gradient to produce a motion phase sensitizing field gradient $\vec{F}$ which imparts a second phase component in the FID signal that indicates the motion of the gyromagnetic material which is producing the FID signal; and*

*processor means for receiving such sensed FID signal and separating the phase component therein indicative of gyromagnetic material position from the phase component therein indicative of gyromagnetic material motion such that accurate images may be reconstructed therefrom.*

*19. The NMR scanner as recited in claim 18 in which the means for generating the motion sensitizing field gradient $\vec{F}$ includes control means for producing the field $\vec{F}$ over a period 2T after application of the excitation magnetic field $B_1$ and the polarity of the field gradient $\vec{F}$ alternates with respect to the gyromagnetic material such that the integral of the field gradient $\vec{F}$ over the time period 2T is substantially zero.*

*20. The NMR scanner as recited in claim 18 which includes control means for cyclically generating a series of said FID signals, said control means including:*

*means for altering the position field gradient $\vec{G}$ during successive cycles to produce a series of FID signals indicative of the gyromagnetic material at a succession of different locations.*

*21. The NMR scanner as recited in claim 20 in which the processor means performs an inverse Fourier transform on the series of sensed FID signals.*

*22. The NMR scanner as recited in claim 20 in which a plurality of cycles are performed for each value of the position field gradient $\vec{G}$ and the value of the motion field gradient $\vec{F}$ is altered during each of said plurality of cycles.*

*23. The NMR scanner as recited in claim 19 in which the phase component in the FID signal due to motion is a function of the magnitude of the motion field gradient $\vec{F}$, the duration of period 2T and the magnitude of the motion in the direction of the field gradient $\vec{F}$, and in which the phase component in the FID signal due to position is a function of the integral of the position field gradient $\vec{G}$ over the time period between generation of the excitation magnetic field $B_1$ and the specific sampling time during the sensing of the FID signal.*

*24. An NMR scanner for producing an image, the combination comprising:*

*means for generating a polarizing magnetic field $B_0$ within a gyromagnetic material;*

*means for applying an excitation magnetic field $B_1$ to the gyromagnetic material which produces a transverse magnetic moment in the gyromagnetic material;*

*means for sensing both the amplitude and phase of a FID signal produced by the gyromagnetic material excited by said excitation magnetic field $B_1$;*

*means for generating a position field gradient $\vec{G}$ which position sensitizes the FID signal to indicate the position of the gyromagnetic material which is producing the FID signal;*

*means for generating a motion field gradient $\vec{F}$ which is applied to the gyromagnetic material for a period of time from zero to 2T after the application of the excitation magnetic field $B_1$ and prior to the production of the FID signal, and wherein the motion field gradient F alternates in polarity with respect to the gyromagnetic material at least twice during said time period and the integral of the motion field gradient $\vec{F}$ over said time period is substantially zero; and*

*processor means for receiving the sensed FID signal and producing data which is employed to reconstruct an image.*

*25. The NMR scanner as recited in claim 24 in which the motion field gradient $\vec{F}$ is substantially anti-symmetrical with respect to time T during said time period.*

*26. The NMR scanner as recited in claim 24 in which the motion field gradient $\vec{F}$ is substantially symmetrical with respect to time T during said time period.*

*27. The NMR scanner as recited in claim 24 in which the image reconstructed from said data indicates the density of said gyromagnetic material at the positions indicated by the position sensitized FID signals.*

*28. In a gyromagnetic resonance instrument for producing an image of an extended subject which contains both stationary gyromagnetic material and moving gyromagnetic material, in which the instrument performs a cycle with a measurement period between the time of initial excitation $T_A$ and the time of FID acquisition $T_B$ by applying a transverse excitation field to the gyromagnetic material to thereby impart a transverse excited magnetization therein, and receiving a FID signal responsive to the transverse excited magnetization, the improvement comprising:*

*means for applying a magnetic field gradient to the gyromagnetic material during a cycle such that the FID signal which is received is both position and motion sensitized in accordance with the following expression:*

$$S(t)=\int\int M_1(r,v)e^{2\pi i\gamma[\vec{G}\cdot\vec{r}+\vec{F}\cdot\vec{v}(T)^2]}drdv$$

*wherein $\vec{F}$ is the element of the field gradient which is applied during the measurement period for a time 2T, which has alternating polarity with respect to the gyromagnetic material and which has a first integral over the time 2T of zero;*

*wherein $\vec{G}$ is the element of the field gradient which is applied during the cycle; and which has a first integral over the cycle which is not zero;*

*wherein phase factor $\vec{r}$ is the average position vector during the time when the $\vec{G}$ element of the field gradient is actively applied;*

*wherein phase factor $\vec{v}$ is the average motion vector during the time when the $\vec{F}$ element of the field gradient is actively applied; and*

*wherein $M_1(r,v)$ is the gyromagnetic material density of a resolvable volume located at r and having the motion v;*

*detector means for receiving the FID signal S(t) and producing therefrom a signal $S_1(t)$ which is phase-coherently referenced to the cosine-phase of the transverse excitation field and a signal $S_2(t)$ which is phase-coherently referenced to the sine-phase of the transverse excitation field; and*

*processor means for performing an inverse Fourier transform on the complex-pair represented by $S_1(t)+iS_2(t)$ to produce $p_o(r)$ from which an image is reconstructed that indicates the density of the gyromagnetic material.*

*29. The gyromagnetic resonance instrument as recited in claim 28 in which said processor means also produces data $p_0(r,v)$ from which an image is reconstructed that indicates the density of the gyromagnetic material, modulated by the resolvable volume average value of motion in the direction of the magnetic field gradient producing the $\vec{F}$ element.*

*30. The gyromagnetic resonance instrument as recited in claim 28 in which the $\vec{F}$ element of the field gradient alternates in polarity a plurality of times during the period 2T.*

* * * * *